Figure 1:
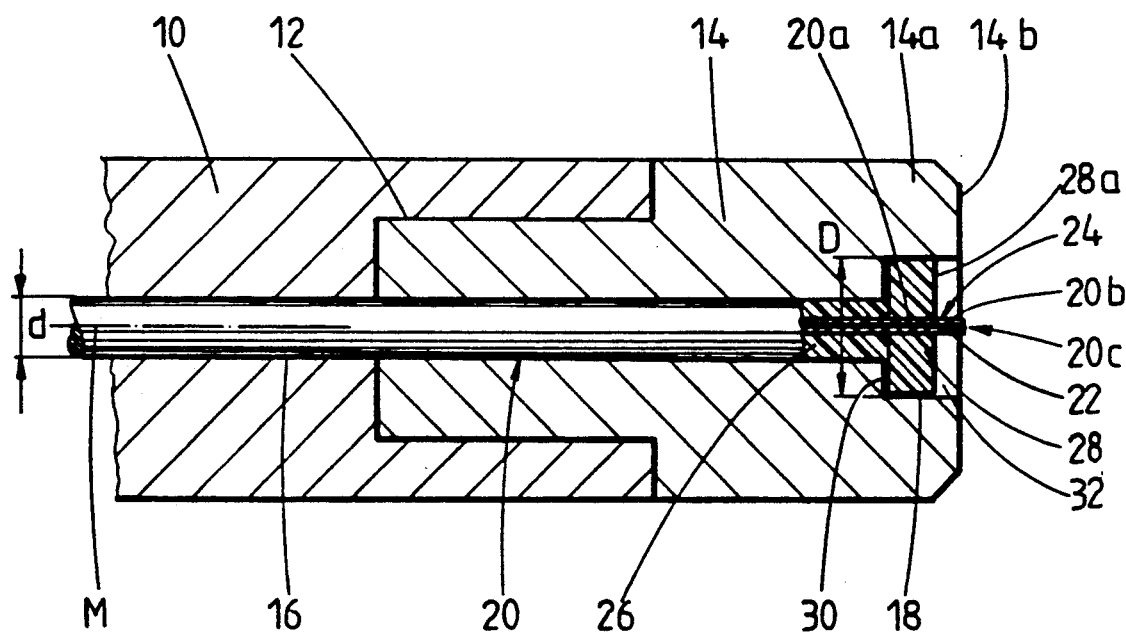

United States Patent [19]
Rhoese

[11] Patent Number: 5,081,694
[45] Date of Patent: Jan. 14, 1992

[54] PLUG FOR FIBER-OPTIC WAVEGUIDES

[75] Inventor: Hartmut Rhoese, Wuppertal, Fed. Rep. of Germany

[73] Assignee: Souriau Electric GmbH, Erkrath, Fed. Rep. of Germany

[21] Appl. No.: 551,872

[22] Filed: Jul. 12, 1990

[30] Foreign Application Priority Data

Jul. 15, 1989 [DE] Fed. Rep. of Germany ....... 3923465

[51] Int. Cl.⁵ .......................... G02B 6/00; G02B 6/36
[52] U.S. Cl. ............................................. 385/53
[58] Field of Search ................ 350/96.20, 96.21, 96.22

[56] References Cited

U.S. PATENT DOCUMENTS

| 4,190,317 | 2/1980 | Makuch | 350/96.20 |
| 4,409,815 | 10/1983 | Burkel et al. | 350/96.20 X |
| 4,730,889 | 3/1988 | Becker et al. | 350/96.21 X |
| 4,848,866 | 7/1989 | Feulner et al. | 350/96.20 |

FOREIGN PATENT DOCUMENTS

| 2812284A1 | 9/1978 | Fed. Rep. of Germany . |
| 3005918 | 9/1981 | Fed. Rep. of Germany . |
| 2516858C2 | 1/1983 | Fed. Rep. of Germany . |

*Primary Examiner*—Akm Ullah
*Attorney, Agent, or Firm*—John F. A. Earley; John F. A. Earley, III

[57] ABSTRACT

Plug for fiber-optic waveguide with an optically active core, a jacket surrounding the core, as well as an outer coating arranged around it for detachable coupling to electro-optical components emitting high-energy laser light.

9 Claims, 1 Drawing Sheet

PLUG FOR FIBER-OPTIC WAVEGUIDES

Fiber-optic waveguides have been increasingly used in recent years for terrestrial communication, but also for, e.g., microsurgery. The optical waveguides are often used as guides for laser light, which enters into the optical waveguide after appropriate focusing.

This implies that the end face of the optical waveguide must be located at the focal point of the corresponding lens system in order to achieve the most complete energy transmission possible. For this purpose, it is also necessary to have an optical waveguide with an absolutely flat end face in order to prevent scattered rays and reflections from occurring insofar as possible. Plugs which have a central axial passage channel in which the optical waveguide is arranged have been known for this purpose. After placement of the fiber, its free end face is ground flat together with the end face of the plug tip.

Especially when fiber-optic waveguides are used for high-energy applications, e.g., for treating materials or in medical engineering, where energies in the mW to W range must be transmitted, the use of the above-described plug involves the risk of burnoff losses at the point of transition of the focused laser light to the optical waveguide because of the high energies being transmitted, due to oblique incident light components or reflections. These burnoff losses occur mainly in the area of the polymer jacket surrounding the optically active fiber core, which (jacket) in turn is usually surrounded by an outer coating in order to impart a certain flexibility to the fiber as a whole, as is necessary, for example, for application for endoscopy. The consequence of such burnoff losses is that reliable energy transmission can no longer be guaranteed, and the plug with the optical waveguide connected to it must be replaced. Therefore, the object of the present invention is to provide a plug for the application specified in the introduction, with which the above-described disadvantages can be prevented form occurring. The plug shall preferably be designed such that it can also be used for one-time applications, which frequently occur in medical engineering, where the corresponding endoscopes are discarded after an operation for hygienic reasons.

The present invention is based on the discovery that the above-described burnoff losses in the area of the jacket of the optical waveguide are due mainly to the lack of sufficient heat removal in a prior art plug because of the "closed installation" of the optical waveguide, as a consequence of which cooling must be provided for the fiber. It was also recognized in the present invention that external cooling, e.g., via a cooling unit, is practically impossible for technical reasons, because the optical waveguide section to be cooled, which has a diameter of, e.g., 0.5 mm and a length of a few mm, is too small to lend itself to selective cooling by means of a cooling unit.

All the more surprising is the new discovery that the desired cooling can be achieved in an amazingly simple manner by removing the coating from the free end zone of the fiber, so that it now consists only of the optically active core and a thin jacket surrounding same, and this free end section is arranged such that it has no direct contact with the passage opening in the plug or its end face. In other words, the free end zone of the fiber will now reach freely over the passage channel or the corresponding parts used to position the optical waveguide.

It was surprisingly found that a free, projecting optical waveguide section of ca. 1 mm is sufficient to completely prevent the above-described burnoff losses from occurring, because the freely exposed end of the optical waveguide permits unhindered radiation of light waves and consequently of energy from the polymer jacket into the surroundings.

Thus, the invention pertains to a plug for a fiber-optic waveguide with an optically active core, a polymer jacket surrounding said core, as well as an outer coating surrounding it for detachable coupling to electro-optical components emitting high-energy laser light, with the following characteristics:

the plug has a plug housing, an axial passage channel and, if desired, positioning means for receiving and fixing the optical waveguide, are arranged in the plug housing, the optical waveguide extends to the area of the plug tip, the optical waveguide is designed without outer coating at its free end, the free end of the optical waveguide is arranged at a spaced location from the wall of the passage channel and/or it projects over the passage channel or the corresponding positioning means.

In the simplest case, the plug would differ from a prior art plug in that the free end of the optically active core with the associated jacket projects over the end face of the plug tip. Even though the basic idea of the present invention is realized with such an embodiment, there is a risk that the projecting tip of the optical waveguide would break off during the use of such a plug.

Therefore, it is proposed according to an advantageous embodiment that the optical waveguide be arranged such that its end face at its free end is flush with the end face of the plug tip or ends a short distance behind it.

Based on the above considerations, all this implies that a hollow space similar to an annular chamber must remain between the circumferential surface of the free end of the fiber and the corresponding wall of the passage channel. This hollow space is realized simply by the corresponding section of the optical waveguide not having any outer coating. However, it may also be advantageous to provide the corresponding end face section of the passage channel with a wider opening, especially when a centering element for the optical waveguide is arranged in this zone.

Such a centering element is preferably used in order to guarantee reliable and accurate positioning of the fiber in the plug and accurate coordination of the end face of the fiber with the focal point of the laser light to be absorbed.

The centering element is now arranged displaced toward the free end face of the plug tip, while the tip of the fiber projects over it and ends just before or is flush with the end face of the plug tip. Thus, the end face of the tip of the plug can also be used to position the plug on a corresponding electro-optical component.

The optical waveguide section held by the centering element can also now be designed without outer coating, while the optical waveguide section located behind it, in the passage channel of the plug, may be designed in the usual manner. In this embodiment, the centering element is also used for additional cooling of the front section of the optical waveguide and it preferably consists, for this purpose, of a material with good thermal conductivity.

For example, for medical applications, such as endoscopy, the optically active core of the optical waveguide has a diameter of less than 0.5 mm. The jacket surrounding the core, which consists especially of a polymer, but which may also consist of other materials, e.g., glasses, has a thickness of only a few microns. Together with the outer coating, an overall diameter of about one mm will be obtained. In this case, it is sufficient to have the free end section of the optical waveguide freely project by about one mm in the above-described manner. As a result, light waves with a relatively steep incidence angle can be emitted unhindered into the free surrounding space through the jacket, while the light waves with relatively flat incidence angles are readily totally reflected in the rear zone of the optical waveguide in the interfacial zone between the optically active core and the polymer jacket surrounding same. The principle of fiber-optic waveguides is ultimately based on this.

The plug itself preferably consists of metal, and the optical waveguide is fixed on the plug housing by, e.g., crimping, and the crimped area is to be provided in an area of the waveguide in which the waveguide has an outer coating in order to prevent deformation of the polymer jacket or the optically active core.

The end face of the free end of the optical waveguide must, of course, be absolutely flat insofar as possible in this case as well in order to prevent scattered rays. Flat grinding together with the end face of the plug tip is ruled out here, because the brittle waveguide freely projects over the associated components of the plug and would break off. However, it was surprisingly found that an absolutely flat end face can also be obtained by simple breaking.

Further characteristics of the present invention will appear from the characteristics of the subclaims as well as the other application documents.

The present invention will be explained below in greater detail on the basis of an exemplified embodiment, and the single figure shows a highly schematic sectional representation of a plug with an inserted fiber-optic waveguide.

To insure greater clarity, the rear part of plug 10, which is of no interest here, is not shown. The front part of said plug 10, which is the part on the right in the figure, consists of metal and has an inwardly extending bore 12 on its end face, into which a plug tip 14 is rigidly inserted.

A passage channel 16 with circular cross section is arranged coaxially to the longitudinal center line M in said plug 10 as well as in the plug tip. Said passage channel has a diameter d. Toward the front end, which is on the right in the figure, said passage channel 16 has an increased internal diameter D. Thus, said plug 10 has a pot-shaped recess 18 in the area of the free end 14a of said plug tip 14.

A fiber-optic waveguide 20 is arranged in said passage channel 16. This consists of an optically active glass fiber core 22 with a diameter of ca. 0.5 mm and a thin polymer jacket 24 surrounding said core 22, as well as a coating 26 arranged around it, which consists, e.g., of a plastic.

Said optical waveguide 20 is crimped onto the plug housing at the left-hand end of said plug 10 and extends along said passage channel 16 into the area of the end face 14b of said plug tip 14.

As is apparent from the figure, the free end section 20a of the optical waveguide, which extends within the pot-shaped recess 18, is freed from the outer coating 26.

In the area of pot-shaped recess 18, a centering element 28 is arranged, which is seated flush there and two-dimensionally surrounds said free end zone 20a of said optical waveguide 20, but only in a partial area, so that said tip 20b of said optical waveguide 20 projects over the end face 28a of said centering element 28. As is also apparent from the figure, the rear surface of said centering element 28 also abuts against the shoulder 30 in the area of said pot-shaped recess 18. Said centering element 28 is cemented into said recess 18 in this case.

The essential characteristic of the plug is that said tip 20b of said optical waveguide 20 has no surface contact with the wall of said passage channel 16 and said recess 18 and it freely projects over said passage channel 16 and said centering element 28, so that a hollow space 32 is formed between said tip 20b and the wall of said recess 18.

The end face 20c of said optical waveguide 20 is made absolutely flat perpendicularly to the longitudinal center line M, by breaking the optically active core 22 at this point, and otherwise it is flush with the end face 14b of said plug tip 14.

As a result, said tip 20b, which is protected by said plug tip 14, is prevented from breaking off even in the case of incorrect use of said plug 10. At the same time, said end face 14b of said plug tip 14 also serves to position the plug in an electro-optical component. The plug is positioned such that the focal point of the laser light emitted and focused by the component is located directly in the center of said end face 20c of said optical waveguide 20.

If light waves with a relatively steep angle happen to penetrate into said tip 20b of said optical waveguide 20 during the use of the device, these are irradiated unhindered into said hollow space 32. Overheating due to reflections is prevented. As a result, burnoff losses due to uncontrollable reflections and a corresponding accumulation of heat in the area of the jacket are prevented from occurring.

I claim:

1. Plug for a fiber-optic waveguide with an optically active glass fiber core, a jacket surrounding the core, and an outer coating arranged around said jacket for detachable coupling to electro-optical components emitting high energy laser light, comprising a plug housing which has an axial passage channel for receiving and fixing the optical waveguide, wherein the optical waveguide is designed without outer coating at its free end and is arranged at a spaced location from the inner wall of the passage channel positioned in the area of the plug tip by a centering element while freely projecting from said centering element and arranged such that its end face at its free end is flush with the end face of the plug tip.

2. Plug in accordance with claim 1, wherein the centering element consists of a material with high strength, but good thermal conductivity.

3. Plug in accordance with claim 1, wherein the centering element (28) is arranged in an expanded section (18) of the passage channel (16), which expanded section is open toward the end face (14b) of the of the plug tip (14), immediately in front of the freely projecting end section (20b) of the optical waveguide (20).

4. Plug in accordance with claim 1, wherein the length of the freely projecting end section (20b) of the optical waveguide (20) is one to five times the diameter of the optical core (22) of the optical waveguide (20).

5. Plug in accordance with claim 1, wherein the centering element consists of ruby.

6. Plug in accordance with claim 1, wherein the centering element consists of nickel-silver.

7. Plug in accordance with claim 1, wherein the plug tip consists of ceramic.

8. A fiber-optic waveguide plug for detachable coupling to electro-optical components emitting high energy laser light, comprising a plug housing having a plug tip portion, the plug tip portion having an end face, the plug housing having an axial passage channel extending through the plug housing to the end face of the plug tip portion, a fiber-optic waveguide mounted in the axial passage channel, the fiber-optic waveguide having an end portion, the fiber-optic waveguide having an optically active glass fiber core, a jacket surrounding the core, and an outer coating surrounding the jacket except at the end portion of the waveguide, and means mounted on the plug tip portion for centering the end portion of the waveguide in the channel, the plug tip portion having a hollow space in the channel surrounding the end portion of the waveguide, and the end portion of the waveguide extending to the end face of the plug tip.

9. The fiber-optic waveguide plug of claim 8, the channel having a wider diameter in the plug tip portion to create the hollow space.

* * * * *